United States Patent
Mehlberg

(10) Patent No.: US 10,238,987 B2
(45) Date of Patent: Mar. 26, 2019

(54) ALKYLATION SYSTEM AND A PROCESS FOR COOLING A VENT STREAM

(71) Applicant: UOP LLC, Des Plaines, IL (US)

(72) Inventor: Robert L. Mehlberg, Wheaton, IL (US)

(73) Assignee: UPO LLC, Des Plaines, IL (US)

(*) Notice: Subject to any disclaimer, the term of this patent is extended or adjusted under 35 U.S.C. 154(b) by 0 days.

(21) Appl. No.: 15/481,268

(22) Filed: Apr. 6, 2017

(65) Prior Publication Data
US 2017/0209807 A1    Jul. 27, 2017

Related U.S. Application Data

(62) Division of application No. 14/597,776, filed on Jan. 15, 2015, which is a division of application No. 12/493,662, filed on Jun. 29, 2009, now Pat. No. 8,937,208.

(51) Int. Cl.
| | |
|---|---|
| *B01D 5/00* | (2006.01) |
| *B01D 3/32* | (2006.01) |
| *C07C 2/66* | (2006.01) |
| *F28D 15/00* | (2006.01) |
| *B01D 3/14* | (2006.01) |
| *B01J 19/24* | (2006.01) |

(52) U.S. Cl.
CPC ............ *B01D 5/0006* (2013.01); *B01D 3/14* (2013.01); *B01D 3/32* (2013.01); *B01D 5/0063* (2013.01); *B01D 5/0078* (2013.01); *B01D 5/0084* (2013.01); *B01J 19/24* (2013.01); *C07C 2/66* (2013.01); *F28D 15/00* (2013.01); *B01J 2219/00103* (2013.01); *B01J 2219/24* (2013.01)

(58) Field of Classification Search
None
See application file for complete search history.

(56) References Cited

U.S. PATENT DOCUMENTS

| | | | | |
|---|---|---|---|---|
| 2,988,894 | A * | 6/1961 | Pool ...................... | B01D 3/14 202/160 |
| 3,159,008 | A * | 12/1964 | Nebgen ................. | F25B 9/002 62/114 |
| 3,309,882 | A * | 3/1967 | Cabanaw ............ | B01D 3/4238 203/2 |
| 3,929,925 | A * | 12/1975 | Chapman ............. | C07C 2/62 585/723 |

OTHER PUBLICATIONS

Seider et al. Heat Transfer Media, Product and Process Design Principles, 3rd Edition, 2009, p. 471. (Year: 2009).*

* cited by examiner

*Primary Examiner* — Philip Y Louie

(57) ABSTRACT

One exemplary embodiment can be a process for cooling a vent stream from a receiver. Generally, the process may include providing a refrigerant including at least one compound contained in the receiver so the refrigerant leaking into the receiver can be compatible with the process.

4 Claims, 1 Drawing Sheet

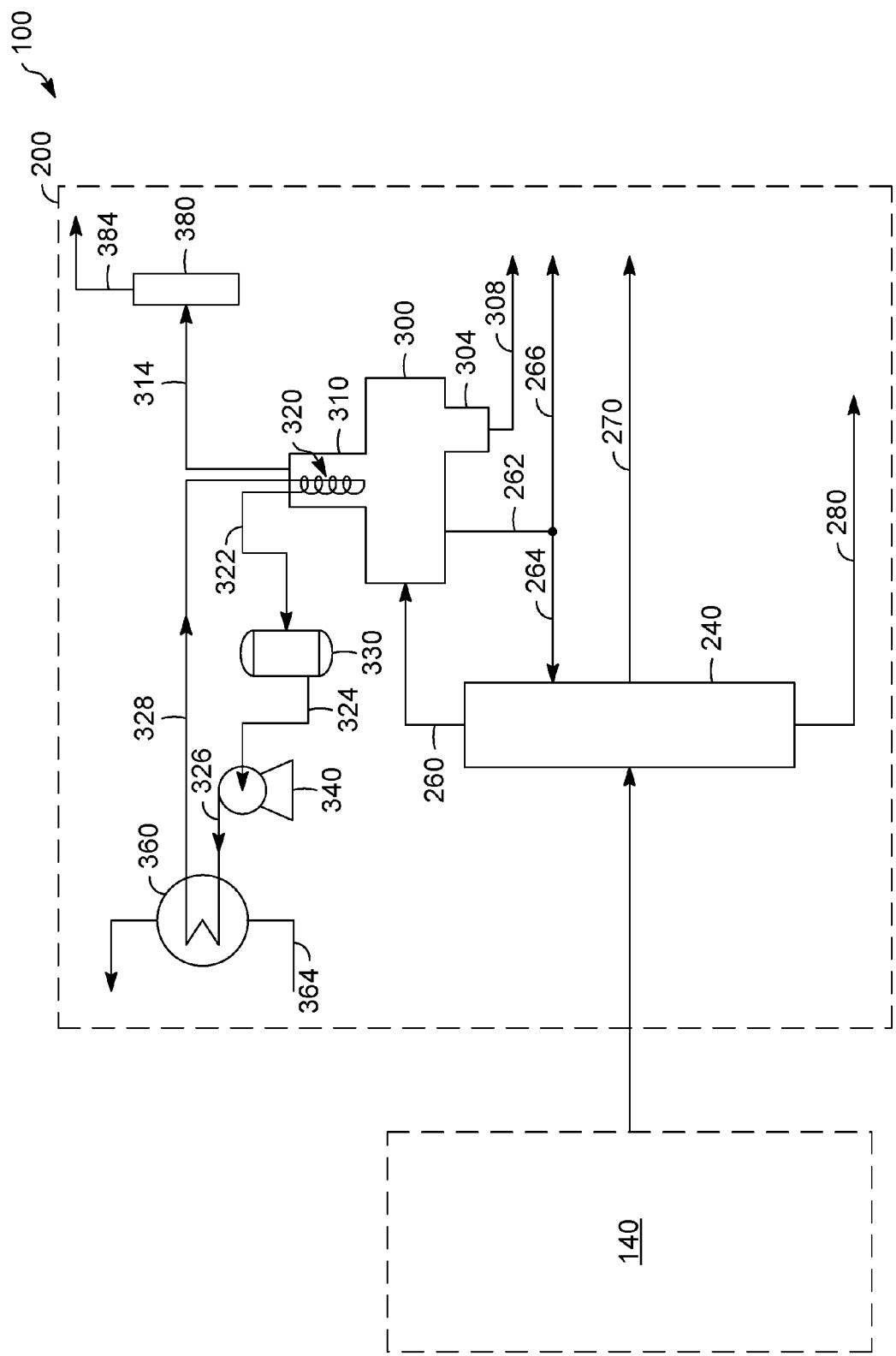

ALKYLATION SYSTEM AND A PROCESS FOR COOLING A VENT STREAM

CROSS-REFERENCE TO RELATED APPLICATION

This application is a Division of copending application Ser. No. 14/597,776 filed Jan. 15, 2015, which application is a Division of application Ser. No. 12/493,662 filed Jun. 29, 2009, now U.S. Pat. No. 8,937,208, the contents of which cited applications are hereby incorporated by reference in their entirety.

FIELD OF THE INVENTION

This invention generally relates to an alkylation system, and a process for cooling a vent stream from a receiver of a depropanizer column in the system.

DESCRIPTION OF THE RELATED ART

Often a fractionation zone is positioned downstream of an acid alkylation unit to separate the hydrocarbons into various streams and any remaining acid. In the fractionation zone, often one or more columns are utilized for providing these separate streams. Usually, the first column in the series receiving the alkylation zone effluent provides an overhead stream that can include light hydrocarbons and the acid. Often, the acid can be recycled back to the alkylation unit.

In the receiver of the first column, a chiller can be provided to cool vent gas exiting the receiver. Often a light hydrocarbon can be used as a refrigerant to cool the vent gas.

Typically, the vent gas is at a higher pressure than the refrigerant within the coils. As a consequence, the acid alkylation catalyst can leak into the refrigerant system. As a result, the acid can corrode equipment and lines, such as the refrigerant compressor. Replacing the compressor and other equipment can incur costs and increase hazards. Thus, it would be desirable to eliminate this risk and lower operating costs.

SUMMARY OF THE INVENTION

One exemplary embodiment can be a process for cooling a vent stream from a receiver. Generally, the process may include providing a refrigerant including at least one compound contained in the receiver so the refrigerant leaking into the receiver can be compatible with the process.

Another exemplary embodiment may be an alkylation system. Generally, the alkylation system may include an acid alkylation zone and a fractionation zone. Usually, the fractionation zone has a depropanizer column, which can include a receiver. The receiver can include a vent condenser containing one or more cooling coils, which may contain a refrigerant at a pressure greater than the pressure in the receiver.

Yet another embodiment can include a process for cooling a vent stream from a receiver of a depropanizer column in an acid alkylation unit. Generally, the process includes providing a refrigerant including propane to one or more cooling coils contained in a vent condenser of the receiver. Typically, the propane in the one or more cooling coils is at a pressure greater than the receiver.

The embodiments provided herein can provide a refrigerant at a higher pressure than the gases in the receiver. Typically, leaks can happen due to cracking of the one or more cooling coils. As a result, the refrigerant can leak into the process rather than the vent gases leaking into the one or more cooling coils. Typically, the refrigerant can be selected from a light hydrocarbon that is compatible with the process, such as propane, so any leak from the refrigerant into the vent system can simply be processed along with the other fluids. Particularly, the refrigerant can be compatible with the overall fractionation zone fluids so as to be merely separated along with the other products.

Definitions

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$ . . . $Cn$ where "n" represents the number of carbon atoms in the one or more hydrocarbon molecules. Additionally, characterizing a stream as, e.g., a "vent stream", can mean a stream rich in one or more substances representative of the characterizing adjective, such as a vent stream being rich in at least one fluid typically present in a receiver.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by mole, of a compound or class of compounds in a stream or an effluent.

As used herein, the term "substantially" can mean an amount of at least generally about 80%, preferably about 90%, and optimally about 99%, by mole, of a compound or class of compounds in a stream or an effluent.

As used herein, the term "vapor" can mean at least one of a gas or a dispersion that may include or consist of one or more hydrocarbons.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$. In some preferred embodiments, a substantially anhydrous hydrogen fluoride can be utilized.

As depicted, process flow lines in the figures can be referred to as lines, effluents, or streams. Particularly, a line can contain one or more effluents or streams, and one or more effluents and streams can be contained by a line.

BRIEF DESCRIPTION OF THE DRAWING

The FIGURE is a schematic depiction of an exemplary alkylation system or unit.

DETAILED DESCRIPTION

Referring to the FIGURE, an acid alkylation system or unit 100 can include an acid alkylation zone 140 and a fractionation zone 200. Typically, the acid alkylation zone 140 can be any suitable alkylation zone, typically utilizing an acid alkylation catalyst. Usually, the acid alkylation catalyst can include a hydrogen fluoride. Exemplary alkylation zones are disclosed in, e.g., U.S. Pat. No. 5,098,668.

The fractionation zone 200 can include one or more distillation columns, such as a depropanizer column 240. Exemplary distillation columns of the fractionation zone 200 are disclosed in, e.g., U.S. Pat. No. 4,348,544. The depropanizer column 240 can provide an overhead stream 260, a side-stream 270, and a bottom stream 280. Usually, the side-stream 270 can include or be rich in one or more hydrocarbons, such as $C_3$-$C_5$ hydrocarbons, more typically, $C_4$ hydrocarbons. The bottom stream 280 can include or be rich in $C_4^+$ hydrocarbons, typically an alkylate product. The overhead stream 260 can include or be rich in one or more $C_4^-$ hydrocarbons and an alkylation catalyst, typically an acid such as hydrogen fluoride. The overhead stream 260 can be received within a receiver 300 forming a boot 304. The boot 304 can collect an alkylation catalyst and provide an alkylation catalyst stream 308 that can be recycled to the acid alkylation zone 140.

The receiver 300 can also provide a hydrocarbon product in a stream 262 that can be split into a reflux stream 264 sent back to the depropanizer column 240 and an overhead product stream 266, typically including propane. In addition, the receiver 300 can form a vent condenser or a stack 310 that can provide a vent stream 314 including $C_2^-$ hydrocarbons with a reduced level of an acid alkylation catalyst. The vent stream 314 can be provided to a scrubber 380 to provide a scrubber effluent stream 384 that can be sent to any suitable destination, such as fuel gas or the flare. Typically, the receiver 300 can be at a pressure of no more than about 1,720 kPa.

In the vent condenser 310, one or more cooling coils 320 can be provided to cool the vent stream 314 prior to exiting the vent condenser 310 to partially recover propane and the acid alkylation catalyst. Typically, the one or more cooling coils 320 can contain at least a portion of the refrigerant, and the refrigerant can be at a pressure greater than the pressure in the receiver 300. The vent stream 314 can be at a temperature of no more than about −20° C. and a pressure of no more than about 1,720 kPa. The refrigerant can enter the one or more cooling coils 320 and then exit in a line 322.

Typically, the one or more cooling coils 320 can include any suitable refrigerant, such as an olefin or a paraffin, in a liquid phase. Usually, a suitable olefin can include a $C_2$-$C_4$ olefin, and a suitable paraffin can include propane. Preferably, the refrigerant can be a dry propane obtained from, e.g., a propane stripper or a product dryer, chilled, and pumped to about 60 to about 140 kPa above the pressure in the receiver 300. In the event of a coil leak, the high-pressure cold propane as the working fluid in the vent condenser 310 can leak into the depropanizer column 240, rather than the alkylation catalyst leaking into the one or more cooling coils 320. Hence, the alkylation catalyst, typically hydrogen fluoride, cannot contaminate the wet gas or fuel systems. Moreover, a leak can be detected quickly and fixed by monitoring the refrigerant level in the one or more cooling coils 320 or a surge drum 330.

The line 322 can communicate with the surge drum 330. The refrigerant can pass through a line 324 to a pump 340, which can pump the refrigerant up to a pressure of about 1,900 kPa.

Afterwards, the refrigerant can pass through a line 326 to the exchanger 360. Chilling can be provided by vaporizing the same or different refrigerant. Typically, a liquefied petroleum gas stream 364 at a pressure of about 300 to about 500 kPa and a temperature of about −5° to about 5° C. can be provided to cool the vaporized refrigerant. After exiting the exchanger 360, the refrigerant can be at a temperature of no more than about 20° C., preferably below about 0° C. The refrigerant may return to the vent condenser 310 via a line 328.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for cooling a vent stream from a receiver of a depropanizer column in an acid alkylation zone, comprising providing a refrigerant comprising propane to one or more cooling coils contained in a vent condenser of the receiver wherein the propane in the one or more cooling coils is at a pressure greater than the receiver, pumping the refrigerant with a pump and chilling the refrigerant in an exchanger before entering the one or more cooling coils.

2. The process according to claim 1, wherein the refrigerant in the one or more cooling coils is at a temperature of no more than about −30° C.

3. The process according to claim 1, wherein the receiver is at a pressure of no more than about 1,720 kPa.

4. The process according to claim 1, further comprising sending the refrigerant contained in the one or more cooling coils to a pump.

* * * * *